US00PP37220P3

(12) United States Plant Patent
Bacon et al.

(10) Patent No.: US PP37,220 P3
(45) Date of Patent: Jan. 20, 2026

(54) GRAPEVINE PLANT NAMED 'SUGRA64'

(50) Latin Name: *Vitis vinifera*
Varietal Denomination: SUGRA64

(71) Applicant: Sun World International, LLC, Wasco, CA (US)

(72) Inventors: Terry A. Bacon, Maplewood, NJ (US); Terrence J. Frett, Bakersfield, CA (US)

(73) Assignee: Sun World International, LLC, Wasco, CA (US)

( * ) Notice: Subject to any disclaimer, the term of this patent is extended or adjusted under 35 U.S.C. 154(b) by 0 days.

(21) Appl. No.: 19/041,440

(22) Filed: Jan. 30, 2025

(65) Prior Publication Data

US 2025/0301927 P1 Sep. 25, 2025

(30) Foreign Application Priority Data

Mar. 22, 2024 (PE) ..... 541-2024/DIN

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205, 206, 207
See application file for complete search history.

*Primary Examiner* — Susan Mccormick Ewoldt
(74) *Attorney, Agent, or Firm* — Knobbe, Martens, Olson & Bear, LLP

(57) ABSTRACT

The new variety of grapevine 'SUGRA64' is characterized by the production of a large-sized, dark red and obtuse ovoid berry with an early season ripening date. The berries of 'SUGRA64' are firm and very juicy.

1 Drawing Sheet

Latin name of the genus and species claimed: *Vitis vinifera.*

Variety denomination: 'SUGRA64'.

CROSS-REFERENCE TO RELATED APPLICATIONS

This application claims the benefit of Peruvian Application No. 541-2024/DIN, filed on Mar. 22, 2024, which is incorporated by reference herein in its entirety.

BACKGROUND AND SUMMARY

This application relates to the discovery and asexual propagation of a new and distinct variety of grapevine, 'SUGRA64', as herein described and illustrated. The new variety was first selected as breeder number 'GR1009R' by Terry A. Bacon and Terrence J. Frett in Wasco, Kern County, California in August 2020. The variety was originated by controlled hybridization.

The new variety 'SUGRA64' is characterized by the production of a large-sized, dark red and obtuse ovoid berry with an early season ripening date. The berries of 'SUGRA64' are firm and very juicy.

The seed parent is 'Sugrathirtyfive' (U.S. Plant Pat. No. 20,491) and the pollen parent is 'Sugrafiftyfive' (U.S. Plant Pat. No. 30,935). The parent varieties were first crossed in April 2016. The date of first sowing is March 2017, and the date of first flowering is April 2018.

The new variety 'SUGRA64' was first asexually propagated in December 2020 in Wasco, Kern County, California, by Terry A. Bacon and Terrence J. Frett using hardwood cuttings.

The fruit of the new variety 'SUGRA64' is distinguished from its seed parent 'Sugrathirtyfive' (U.S. Plant Pat. No. 20,491) in that while both have berries with rudimentary seed traces, the new variety 'SUGRA64' has a dark red colored berry compared to a green berry for 'Sugrathirtyfive'. Additionally, the new variety 'SUGRA64' has a smaller berry weight at 7.3 g compared to a berry weight of 9.5 g for 'Sugrathirtyfive'. Further, the fruit of the new variety 'SUGRA64' begins ripening about July 21 compared to September 1 for 'Sugrathirtyfive'.

The new variety 'SUGRA64' is distinguished from its pollen parent 'Sugrafiftyfive' (U.S. Plant Pat. No. 30,935) in that while both have berries with rudimentary seed traces, the new variety 'SUGRA64' has dark red colored berries with an obtuse ovoid shape while 'Sugrafiftyfive' has greyed-purple colored berries with a broad elliptic shape. Additionally, the fruit of the new variety 'SUGRA64' begins ripening about July 21 compared to July 5 for 'Sugrafiftyfive'.

The berries of the new variety 'SUGRA64' have an obtuse ovoid shape and dark-red colored skin, similar to 'SUGRA60' (U.S. Plant Pat. No. 34,697), but the berries of the new variety 'SUGRA64' have a smaller berry weight at 7.3 g compared to 9.5 g for 'SUGRA60'. Additionally, the new variety 'SUGRA64' has a lower cluster weight at 600 g compared to 800 g for 'SUGRA60'.

The berries of the new variety 'SUGRA64' have dark red colored skin like 'Sugrafiftythree' (U.S. Plant Pat. No. 29,768), but the fruit of the new variety 'SUGRA64' begin ripening July 21 compared to June 29 for 'Sugrafiftythree'. Additionally, the berries of the new variety 'SUGRA64' have an obtuse ovoid shape compared to the broad elliptic berry shape of 'Sugrafiftythree'.

The new variety 'SUGRA64' has berries with rudimentary seed traces like 'IFG 68-175' (U.S. Plant Pat. No. 21,664), but the berries of the new variety 'SUGRA64' are dark red colored compared to the red colored berries of 'IFG 68-175'. Additionally, the fruit of the new variety 'SUGRA64' begins ripening about July 21 compared to August 10 for 'IFG 68-175'.

The new variety 'SUGRA64' has been shown to maintain its distinguishing characteristics through successive asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration taken from a 3-year-old plant shows typical specimens of the foliage and fruit of the present new grape variety 'SUGRA64'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, sixth edition, 2015.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to three-year-old 'SUGRA64' plants grown in the vicinity of Wasco, Kern County, California during 2022, and is believed to apply to plants of the variety grown under similar conditions of soil and climate elsewhere.

VINE

General: (Measurements taken on a three-year-old plant).

- *Vine size*.—Large. Height: Approximately 2.0 m. Width: Approximately 2.5 m.
- *Vigor*.—Medium vigor.
- *Density of foliage*.—Dense.
- *Productivity*.—Very productive.
- *Crop load*.—Approximately 30 kg per vine after thinning.
- *Own root*.—Yes.
- *Training method*.—Typically spur pruned leaving about 40 2-bud spurs.
- *Resistance*.—Neither resistance nor susceptibility to particular diseases or pests has been observed in this variety.

Trunk:

- *Shape*.—Stocky.
- *Diameter*.—Approximately 7.1 cm (at 30 cm above the soil line).
- *Straps*.—Short.
- *Surface texture*.—Medium shaggy.
- *Inner and outer bark color*.—Inner bark about Medium Greyed-Orange 166C and weathering to about Dark Greyed-Green 197B in the outer bark.

SHOOTS

Young shoot:

- *Form of tip*.—Wide open.
- *Intensity of anthocyanin coloration of tip*.—Absent or very weak.
- *Density of prostrate hairs on tip*.—Absent or very sparse.
- *Density of erect hairs on tip*.—Absent or very sparse.
- *Color*.—About Dark Green 139B and Dark Green 139C.

Woody shoot (observations made in the middle third of shoot):

- *Attitude before tying*.—Semi-drooping.
- *Growth of axillary shoots*.—Strong, about 19 cm to 25 cm in length.
- *Internode length*.—Short, approximately 73 mm.
- *Width at node*.—Approximately 10 mm.
- *Cross section*.—Circular.
- *Surface texture*.—Striate.
- *Main color*.—About Medium Greyed-Orange 166D.
- *Color of dorsal side of internode*.—About Medium Greyed-Orange 166D.
- *Color of ventral side of internode*.—About Medium Greyed-Orange 166D.
- *Color of dorsal side of node*.—About Medium Greyed-Orange 166D with Medium Greyed-Orange 166B around the bud.
- *Color of ventral side of node*.—About Medium Greyed-Orange 166D with Medium Greyed-Orange 166B around the bud.
- *Density of erect hairs on nodes*.—Absent.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 3 mm.
- *Color*.—About Medium Green 141C.
- *Form*.—Bifurcated.
- *Number of consecutive tendrils*.—About 2.
- *Length of tendril*.—Medium, approximately 18 cm.

LEAVES

Young leaves:

- *Color of upper surface of first 4 distal unfolded leaves*.—About Medium Green 143A.
- *Average intensity of anthocyanin coloration of six distal leaves prior to flowering*.—Absent or very slight.
- *Density of prostrate hairs between veins at lower surface of $4^{th}$ distal unfolded leaf*.—Absent or very sparse.

*Density of erect hairs between veins at lower surface of 4th distal unfolded leaf.*—Absent or very sparse.
*Density of prostrate hairs on veins at lower surface of 4th distal unfolded leaf.*—Absent or very sparse.
*Density of erect hairs on veins at lower surface of 4th distal unfolded leaf.*—Absent or very sparse.

Mature leaves (observations made on leaves in the middle third of shoot):
*Size.*—Large.
*Average length.*—Approximately 11 cm.
*Average width.*—Approximately 15 cm.
*Shape of blade.*—Pentagonal.
*Number of lobes.*—Approximately 5.
*Mature leaf profile.*—Undulate.
*Blistering surface of blade upper surface.*—Absent or very weak.
*Leaf blade tip.*—In the plane of the leaf.
*Undulation of margin.*—Slightly undulating.
*Thickness.*—Average-typical of *Vitis vinifera* species.
*Overall shape of teeth.*—Mixture of both sides straight and both sides convex.
*Length of teeth.*—Medium, ranging from about 4 mm to 10 mm.
*Ratio length/width of teeth.*—Very small, nearly 1:1.
*General shape of petiole sinus lobes.*—Half open.
*Tooth at petiole sinus.*—Absent.
*Petiole sinus limited by veins.*—Absent.
*Shape of upper lateral sinus lobes.*—Open.
*Depth of upper lateral sinuses.*—Shallow, approximately 1 cm to 3 cm.
*Density of prostrate hairs between veins on lower surface of blade.*—Absent to very sparse.
*Density of erect hairs between veins on lower surface of blade.*—Absent to very sparse.
*Density of prostrate hairs on main veins on lower surface of blade.*—Absent to very sparse.
*Density of erect hairs on main veins on lower surface of blade.*—Absent to very sparse.
*Density of prostrate hairs on main veins on upper surface of blade.*—Absent to very sparse.
*Autumn coloration of leaves.*—Usually about Light Green 138B becoming about Medium Grey-Brown 199C.

Upper leaf surface:
*Color.*—About Dark Green 139A.
*Surface texture.*—Smooth.
*Surface appearance.*—Dull.
*Anthocyanin coloration of main veins.*—Absent or very low.

Lower leaf surface:
*Color.*—About Medium Green 135C.
*Surface texture.*—Smooth.
*Surface appearance.*—Dull.
*Anthocyanin coloration of main veins.*—Absent or very low.

Petiole:
*Length of petiole.*—Approximately 7 cm.
*Diameter.*—Approximately 2 mm.
*Length of petiole compared to middle vein.*—Much shorter, 7 cm for the petiole compared to 11 cm for middle vein.
*Density of prostrate hairs on petiole.*—Absent.
*Density of erect hairs on petiole.*—Absent.
*Color.*—About Medium Green 141C.

Buds:
*Shape.*—Conical.
*Size.*—Medium, approximately 3 mm wide×4 mm long.
*Position.*—Slightly held out.
*Bud fruitfulness.*—Basal, mostly fruitful.
*Time of bud burst.*—Medium, approximately March 14th for the southern San Joaquin Valley region of California.

FLOWERS

General:
*Flower type.*—Fully developed stamen and fully developed gynoecium.
*Position of first flowering node.*—Usually 4th to 5th node of current season growth.
*Number of inflorescences per shoot.*—Usually 1.2 per shoot.
*Time of full bloom.*—Approximately May 20th in the southern San Joaquin Valley region of California
*Petal color.*—About Deep Yellowish Green 141B and Strong Yellowish Green 141C.

FRUIT

General:
*Ripening period.*—Early season, beginning about July 21st in the southern San Joaquin Valley region of California.
*Use.*—Fresh market.
*Storage quality.*—Good.

Cluster:
*Form.*—Conical, shouldered.
*Cluster size (peduncle excluded).*—Medium.
*Cluster length (peduncle excluded).*—Approximately 22 cm.
*Cluster width.*—Approximately 15 cm.
*Cluster weight.*—Approximately 600 g.
*Cluster density.*—Medium (loose-full).
*Number of berries.*—Approximately 90 berries after tipping.

Peduncle:
*Length.*—Long, approximately 5 cm.
*Diameter.*—Approximately 4 mm.
*Lignification of peduncle.*—Weak.
*Color.*—About Medium Green 143B.

Berry:
*Size.*—Large, approximately 7.3 g.
*Dimensions.*—Width: Approximately 23 mm. Length: Approximately 25 mm.
*Uniformity of size.*—Uniform.
*Shape.*—Obtuse ovoid.
*Cross section.*—Circular.
*Skin color (without bloom).*—About Medium Purple 92A and Dark Violet N92C.
*Flesh color.*—About Medium Yellow-Green 144C at full ripe. About Dark Red-Purple 59B anthocyanin develops as it becomes past ripe.
*Anthocyanin color of flesh.*—Absent or very weak.
*Bloom (cuticular wax).*—Medium, typical of most commercial *Vitis vinifera.*
*Pedicel length.*—Approximately 10 mm.
*Pedicel thickness.*—Medium, approximately between 1.7 mm to 1.9 mm.

*Berry separation from pedicel*.—Moderately easy.
*Seed traces*.—Rudimentary.
*Berry firmness*.—Moderately Firm.
*Flesh juiciness*.—Very juicy.
*Flesh texture*.—Firm and meaty
*Particular flavor*.—Exotic tropical gumdrop.
*Refractometer test*.—About 18 Brix.
*Juice ph*.—About 3.5.
*Titratable acidity*.—About 0.37%.
*Brix:acid ratio*.—Approximately 21.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Rare.
*Skin sensitivity to sunburn*.—None.

What is claimed is:

1. A new and distinct variety of grapevine plant named 'SUGRA64' substantially as illustrated and described herein.

* * * * *

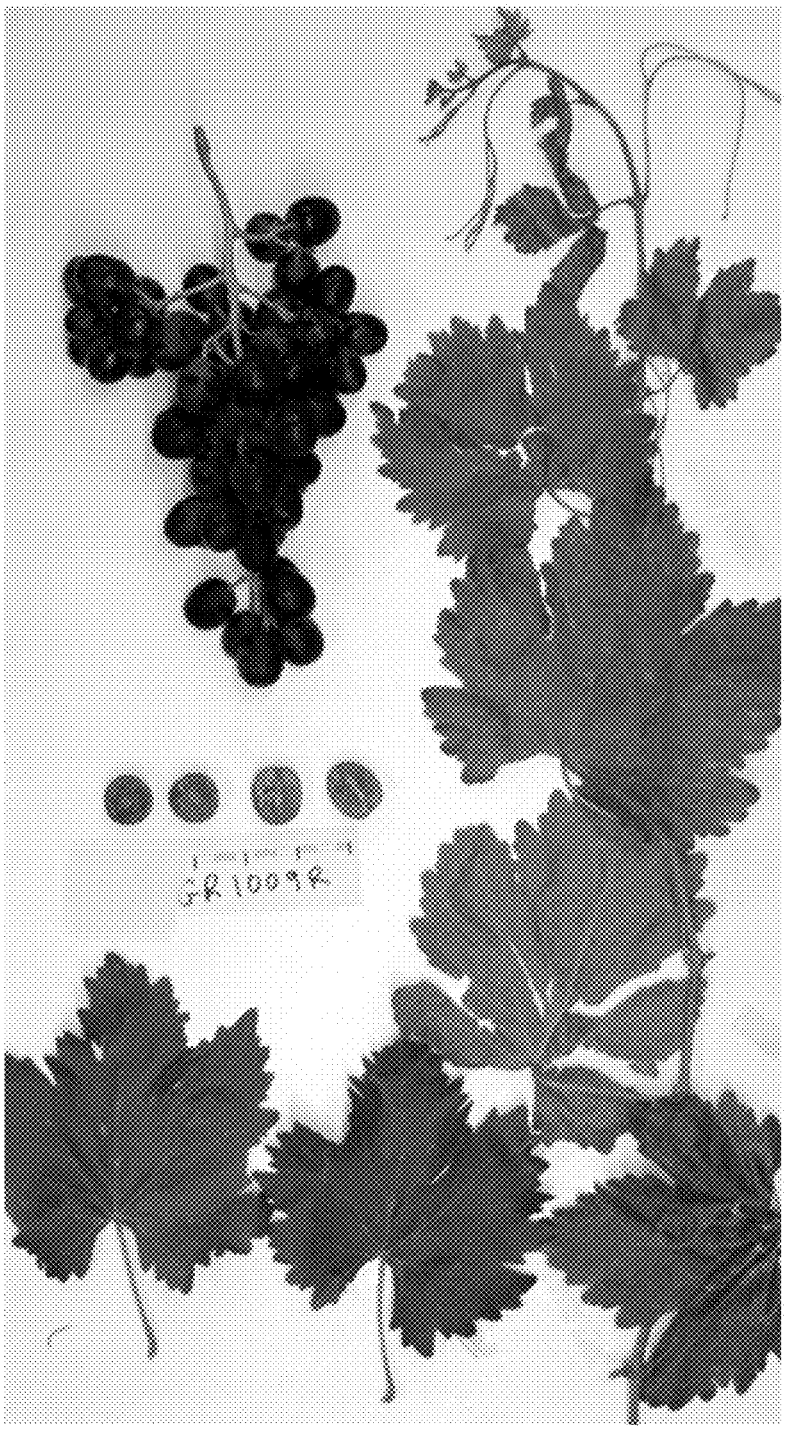
JR 1009R